United States Patent
Utech et al.

(10) Patent No.: US 10,650,925 B2
(45) Date of Patent: May 12, 2020

(54) AUTOMATED UTILIZATION DRIVEN INVENTORY MANAGEMENT

(71) Applicant: CareFusion 303, Inc., San Diego, CA (US)

(72) Inventors: Thomas William Utech, Dallas, TX (US); Maria Consolacion Jaskela, San Rafael, CA (US)

(73) Assignee: CareFusion 303, Inc., San Diego, CA (US)

( * ) Notice: Subject to any disclaimer, the term of this patent is extended or adjusted under 35 U.S.C. 154(b) by 122 days.

(21) Appl. No.: 13/931,746

(22) Filed: Jun. 28, 2013

(65) Prior Publication Data

US 2014/0350952 A1 Nov. 27, 2014

Related U.S. Application Data

(60) Provisional application No. 61/827,419, filed on May 24, 2013.

(51) Int. Cl.
*G16H 40/20* (2018.01)
*G06Q 10/08* (2012.01)

(52) U.S. Cl.
CPC .......... *G16H 40/20* (2018.01); *G06Q 10/087* (2013.01)

(58) Field of Classification Search
CPC .................. G06Q 10/087; G16H 40/20
See application file for complete search history.

(56) References Cited

U.S. PATENT DOCUMENTS 8,666,774 B1 * 3/2014 Gonzales, Jr. ......... G06Q 50/24
                                                        705/2
2002/0032582 A1 * 3/2002 Feeney, Jr. .......... G06F 19/3462
                                                        705/2

(Continued)

FOREIGN PATENT DOCUMENTS

CN          102834142 A      12/2012
KR      1020100049549 A       5/2010
WO    WO-2008157632 A2 *     12/2008 ............. G06Q 50/24

OTHER PUBLICATIONS

International Search Report and Written Opinion of the International Searching Authority for PCT Application No. PCT/US2014/038658, dated Oct. 7, 2014.

(Continued)

*Primary Examiner* — John P Go
(74) *Attorney, Agent, or Firm* — Morgan, Lewis & Bockius LLP

(57) ABSTRACT

Methods for automated inventory management are provided. In one aspect, a method includes receiving storage capability data for an item in a dispensing unit, retrospective usage data for the item in the dispensing unit, and an indicator of a minimum time period for which to stock the item in the dispensing unit. The dispensing unit includes a compartment assigned for storing stock of the item. The method also includes determining, based on the minimum time period for which to stock the item, the storage capability data, and the retrospective usage data, a minimum number of stock of the item to store in the compartment, and providing a notification indicating the determined minimum number of stock of the item to store in the compartment. Systems and machine-readable media are also provided.

21 Claims, 4 Drawing Sheets

(56) References Cited

U.S. PATENT DOCUMENTS

| | | | |
|---|---|---|---|
| 2002/0091594 A1* | 7/2002 | Rosenberg | G06Q 10/087 705/28 |
| 2002/0198624 A1 | 12/2002 | Greenwald et al. | |
| 2006/0249423 A1 | 11/2006 | Reijonen | |
| 2008/0255880 A1* | 10/2008 | Beller | G06Q 10/00 705/3 |
| 2009/0144078 A1 | 6/2009 | Bajars et al. | |
| 2010/0082458 A1* | 4/2010 | Godlewski | G06Q 10/087 705/28 |
| 2010/0161113 A1 | 6/2010 | Tribble et al. | |
| 2010/0174552 A1 | 7/2010 | Hawkes et al. | |
| 2011/0257991 A1 | 10/2011 | Shukla | |
| 2013/0018356 A1 | 1/2013 | Prince et al. | |

OTHER PUBLICATIONS

International Search Report and Written Opinion in PCT Patent Application No. PCT/US2014/039228 dated Aug. 22, 2014, 11 pgs.
"Pandora Analytics," Pandora Healthcare Data Analytics by Omnicell, retrieved from <http://www.omnicell.com/Products/Business_Analytics/Pandora_Analytics.aspx>, retrieved Jul. 10, 2013, pp. 1-4, Omnicell, Inc.
"Welcome to Medacist Solutions Group, LLC," Medacist—The Key to Healthcare Automation, retrieved from <http://www.medacist.com>, retrieved Jul. 10, 2013, 1 page, Medacist Solutions Group, LLC.
Extended European Search Report for Application No. 14801534.0, dated Jan. 30, 2017, 8 pages.
Memo for Mexican Office Action for Application No. MX/a/2015/016104, memo dated Apr. 12, 2017, 2 pages.
Memo concerning Mexican Office Action for Application No. MX/a/2015/016104, memo dated Oct. 11, 2017, 3 pages.
English Memo of Mexican Office Action for Application No. MX/a/2015/016104, memo dated Jan. 24, 2019, 5 pages.
Report of Mexican Office Action for Application No. MX/a/2015/016104, report dated Jul. 17, 2019, 3 pages.
Chinese Office Action for Application No. 201480041984.6, dated Feb. 3, 2019, 13 pages.
United Arab Emirates Office Action for Application No. UAE/P/1568/2015, first received Nov. 21, 2019, 11 pages.
Chinese Office Action for Application No. 201480041984.6, dated Dec. 3, 2019, 15 pages.
European Office Action for Application No. 14801534.0, dated Dec. 13, 2019, 6 pages.

\* cited by examiner

AUTOMATED UTILIZATION DRIVEN INVENTORY MANAGEMENT

CROSS-REFERENCE TO RELATED APPLICATIONS

The present application claims the benefit of priority under 35 U.S.C. § 119 from U.S. Provisional Patent Application Ser. No. 61/827,419 entitled "Automated Utilization Driven Inventory Management," filed on May 24, 2013, the disclosure of which is hereby incorporated by reference in its entirety for all purposes.

BACKGROUND

Field

The present disclosure generally relates to apparatus and methods for supply management and, in particular, relates to controlling the inventory of items in a facility, such as medical items in a health care facility.

Description of the Related Art

It is well known in the medical community, and in particular, in facilities like hospitals, to use an inventory system for dispensing and administering medical items (or "line items"). In this system, medical items provided by a pharmacy, for example, are temporarily stored in a plurality of areas or stations for administration. Many facilities today utilize automated dispensing cabinets ("automated dispensing machines," "ADM," or "dispensing unit") to store medical items and provide decentralized drug distribution to patient care areas. These automated dispensing cabinets provide a wide range of medical items that meet the patient care needs for the patient care area. It is common for as high as 95% of the medication items for patients in a specific care area to be fulfilled by an automated dispensing cabinet.

Hospitals often have limited budgets for procuring medical items in view of the need to maximize staff efficiency to provide patient care. While having medical items closer to patient care areas usually increases efficiency in providing patient care, it creates a challenge in effectively managing all inventory locations for medical items throughout the facility. For instance, a cabinet that fulfills on average 95% of the medication item needs for patients in a specific care area can commonly store at any one time 500 to 750 medical items. In a typical facility having 300 to 350 beds, as many as 11,250 storage locations (e.g., pockets) within multiple cabinets with more than 15,000 items may be needed throughout the facility. This many storage locations can challenge the facility in effectively managing inventory to meet patient care needs and minimize waste through expiration and inventory that is not being utilized (or "turned") based on national benchmark standards.

Current technology provides static PAR levels (e.g., "designated inventory levels," which are boundary markers in inventory levels that signal replenishment is necessary) that drive reorder points for storage locations of automated dispensing cabinets. Typically these designated inventory levels are set at the time an item is assigned to an automated dispensing cabinet. It is difficult, however, to manually select and/or adjust designated inventory levels for different types of medical items, especially in facilities with hundreds or thousands of item types. At such facilities, those with the requisite knowledge to manually select a preferred, subjective inventory level usually do not have the time to set such designated inventory levels for all the different items. Providing a preset designated inventory level value applicable to different types of items is also not beneficial, as different types of items are associated with different types of usage patterns.

Further, usage patterns may vary over time, so that a pre-set designated inventory level that was correct at one time may not be appropriate at a later time. Facilities commonly do not change the designated inventory levels for cabinets in those patient care areas to meet changing usage patterns due to, for example, prescribing pattern changes, seasonal changes, patient mix change, or service line changes. In many instances, this occurs because there are too many storage locations for which the designated inventory level may need to be changed. This leads to waste and ineffective utilization of resources by excessive refill activity, stock-outs, decreased availability of medical items in care areas, and telephone calls between distribution points and the care areas.

SUMMARY

According to certain embodiments of the present disclosure, a system for automated inventory management is provided. The system includes a memory that includes storage capability data and retrospective usage data for an item in a dispensing unit. The dispensing unit includes a compartment assigned for storing stock of the item. The system also includes one or more processors. The one or more processors is configured to receive an indicator of a minimum time period for which to stock an item in the dispensing unit, and determine, based on the minimum time period for which to stock the item, the storage capability data, and the retrospective usage data, a minimum number of stock of the item to store in the compartment. The one or more processors is also configured to provide a notification indicating the determined minimum number of stock of the item to store in the compartment.

According to certain embodiments of the present disclosure, a method for automated inventory management is provided. The method includes receiving storage capability data for an item in a dispensing unit, retrospective usage data for the item in the dispensing unit, and an indicator of a minimum time period for which to stock the item in the dispensing unit. The dispensing unit includes a compartment assigned for storing stock of the item. The method also includes determining, based on the minimum time period for which to stock the item, the storage capability data, and the retrospective usage data, a minimum number of stock of the item to store in the compartment, and providing a notification indicating the determined minimum number of stock of the item to store in the compartment.

According to certain embodiments of the present disclosure, a machine-readable storage medium that includes machine-readable instructions for causing a processor to execute a method for automated inventory management is provided. The method includes receiving storage capability data for an item in a dispensing unit, retrospective usage data for the item in the dispensing unit, and an indicator of a minimum time period for which to stock the item in the dispensing unit. The dispensing unit includes a compartment assigned for storing stock of the item. The method also includes determining, based on the minimum time period for which to stock the item, the storage capability data, and the retrospective usage data, a minimum number of stock of the item to store in the compartment, and providing a notification indicating the determined minimum number of stock of the item to store in the compartment.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

Figure 1:
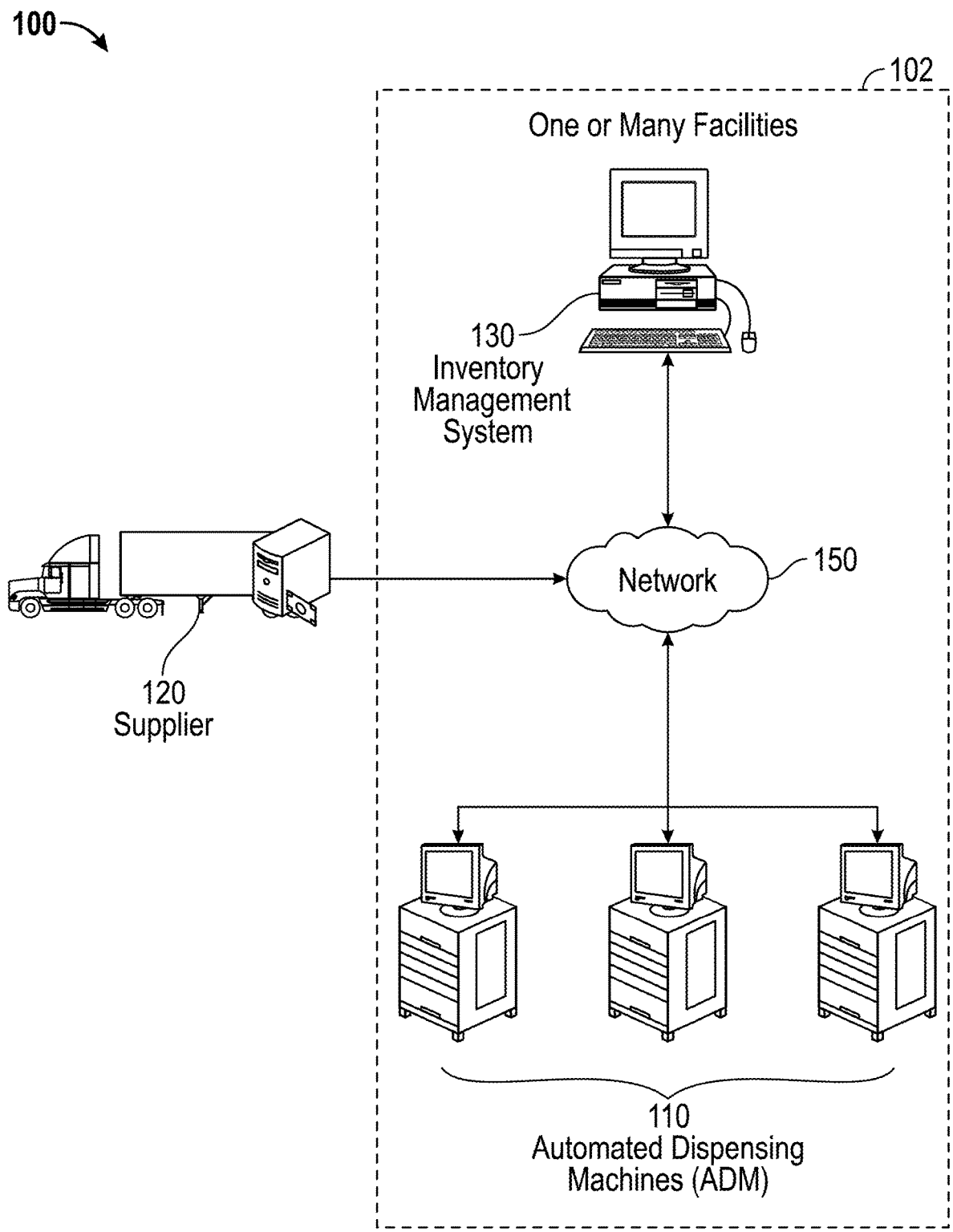
FIG. 1 illustrates an example architecture for automated inventory management.

FIG. 1 illustrates an example architecture 100 for automated inventory management. The architecture 100 includes an inventory management system 130 and ADMs 110 in one or many facilities 102 (e.g., one hospital, several hospital campuses, etc.) connected over a network 150. The network 150 is also connected to a supplier 120 for providing stock of an item to the one or many facilities 102.

Each of the ADMs 110 includes one or many compartments (or "storage spaces") for the storing of items. The compartments in each ADM 110 may vary in size, including compartments having uniform size. The disclosed system can be used with compartments of any size. Each compartment can be measured as a space that has a height, width and length. The space creates a volumetric space that will hold a defined quantity of stock for an item. In certain aspects, the amount of an item that is stored is based on volumetric measurement of the item instead of physical measurement of the item due to a potential variation in how an item is loaded into the compartment, particularly when each individual item has a package with a specific height, width and length. Once the volumetric space of one compartment has been determined, the system can extrapolate the volumetric space of the compartment to larger compartments by increasing volumetric storage based on an increase in proportion size of the larger compartments. Thus, in certain aspects, a user such as a system administrator, pharmacist, or nurse, may start with the smallest sized compartment when determining the first volumetric space for an item and then allow the disclosed system to calculate the volumetric space and corresponding storage capabilities for each larger compartment for the item. In certain aspects, the disclosed system may be configured to assume that the item cannot be placed in a smaller space than the first measured compartment.

A compartment can be defined as open, secure, or controlled. Each type of compartment may offer a different level of security, control, and tracking of items within the compartment. An open compartment has unrestricted access and may be confined by boundaries (e.g., a bin, dividers, or physical marking). If a user has access to the area (e.g., patient room or other patient care area) where the open compartment is located, the user has access to the open compartment and its items. A secure compartment is confined and controlled through limited access to an item. The secure compartment can be a locking compartment that only contains one dose of one item and a user must have authorization to access the locking compartment. A controlled compartment is one that offers access, with appropriate authorization, to one or many doses of one item. The controlled compartment can be a lidded compartment for which a user must provide appropriate authorization to access the compartment.

An ADM 110 may be designated as a centralized store or a distributed store. A centralized store is generally located away from an item use area (e.g., patient care area) and is used for compounding of an item, safety stock of an item, and refill stock for items distributed in certain areas (e.g., patient care areas) and for specific issues (e.g., patient-specific issues). A distributed store is generally located at or near the use area, or alternatively, at a separated/satellite location from a centralized store. Stock of an item that resides in both a centralized store and a distributed store may follow a pattern of measuring forward deployed inventory of the item at the distributed store against the centralized store inventory to determine the appropriate amount of inventory to forward deploy in view of the inventory of the item in the centralized store to provide refills. The total forward deployed inventory quantity may thus be more than the quantity of the item in the centralized store.

Each ADM 110 is connected to the inventory management system 130 over the network 150. The inventory management system 130 provides a facility-wide approach to automatically adjusting stock configuration levels (e.g., PAR levels, minimum and maximum item levels) for items in storage compartments in dispensing units based on changing item utilization. The system evaluates retrospective item utilization data, present item utilization data, and predicted item utilization data in order to automatically suggest and/or set item stock configuration levels using minimum intervention by a user. In certain aspects, the minimum intervention can be accomplished through a system of rules that will automatically, based on specific parameters, adjust item stock configuration levels that fit within the parameters and provide an exception list for those adjustments that fall outside the parameters.

A user such as an administrator or nurse may initially provide the inventory management system 130 with initial system parameters for each item stored in a compartment of the ADMs 110, and at least some of these parameters may be later updated or changed by the inventory management system 130. The initial system parameters may be provided to the inventory management system 130 directly, or provided to one of the ADMs 110 that then provides the user-provided initial system parameters to the inventory management system 130. The initial system parameters include, for example, a maximum number of stock of an item that can fit in a compartment of an ADM 110 ("pocket maximum"), and a minimum number of items that should be stored in a compartment of an ADM 110 ("physical minimum" or "pocket minimum") before additional stock is reordered. The minimum value could be a higher number than what average usage supports, but based on critical need of the item in certain emergent situations, the value would be the minimum amount the facility 102 seeks to keep in the compartment. A compartment is a storage space having a defined area with dimensions of length, width and height. Once a maximum number of stock of an item that can fit in the compartment pocket maximum has been determined, the system can automatically calculate a maximum number of stock of the item that can fit in other compartments based on the other compartment sizes (e.g., based on a percentage increase or decrease in volumetric capacity).

The user may also provide the inventory management system 130 with initial system parameters for a daily average, daily maximum, and inventory philosophy. Alternatively, or additionally, this information can be determined from retrospective item usage data. The daily average is the number of stock of an item from a compartment used per day over a set period of time, and the daily maximum is the maximum number of stock used for any one day of the item from the compartment. The inventory philosophy includes a minimum number of stock of an item ("MIN") required to prevent a stock-out of the item in a compartment. Typically the MIN is a two to three day supply of stock of an item to account for lag time between a scheduled reordering of the item ("refill cycle"). The inventory philosophy also includes a maximum number of stock of the item ("MAX") in the compartment in order to regulate the number of refills of the item in the compartment. Typically the MAX is a five to seven day supply of stock of the item to maximize the utilization of labor to refill the storage locations (e.g., by having a person such as a pharmacy technician refill a specific item in an automated dispensing machine once a week as opposed to every other day). The inventory philosophy further includes a minimum to maximum ratio ("min:max") for determining a number of refills for a storage space for a set time period (e.g., per month).

By way of example only, a user may provide initial system parameters to the inventory management system 130 for storage of a particular item in a specific compartment by first providing a pocket maximum. The pocket maximum is identified by determining the amount of the item that can fit in the compartment. Upon providing the pocket maximum for the compartment to the inventory management system 130, the inventory management system 130 may automatically calculate and populate pocket maximum numbers for other defined storage spaces for the item based on dimensions and percentage of volumetric space change from the initial defined storage space of the compartment. Next, the user provides a pocket minimum by determining a minimum number of stock for an item that is appropriate for the area in which the compartment is located. The number may vary based on, for example, each patient care area, such that a different pocket minimum may be provided for a user for each area or storage location. In certain aspects, the default pocket minimum value is set to one.

Thereafter, the user provides a minimum value indicative of a number of days for which the item should be in stock in the compartment before the inventory management system 130 will trigger a reorder of the item. The inventory management system 130 permits the minimum value to vary based on where the respective ADM 110 is located (e.g., by patient care area), or by the type of the item (e.g., by medication class). The user also provides a maximum value indicative of a number of days in between refills of the item in the compartment that is efficient for the user based on, for example, staff and cost of the item. The inventory management system 130 permits the maximum value to vary by item cost or item grouping. The user then provides a value indicating a length of time for historical utilization data for the item that will be used to determine stock levels. For example, the value may range from 30 to 90 days of historical utilization information.

Thereafter, the user defines a threshold for a number of days after which an item that has not been removed or utilized from a compartment is to be removed, and a cumulative number of stock of an item issued within a defined timeframe but not stored in the automated dispensing machine 110 that when reached triggers a notification that the item be stored in an automated dispensing machine 110. The user may also provide a schedule by which the inventory management system 130 will run. For example, in certain aspects, the disclosed inventory management system 130 is configured to run a query based on the user provided schedule across a logistic supply chain from point of entry (e.g., a dock) of an item to point of utilization or disposition of the item (e.g., use or administration to a patient). The output of this query will define or otherwise update appropriate inventory levels for each compartment based on the storage location within the facility as described in greater detail below. The inventory management system 130 may be configured to maintain current inventory levels for each compartment upon a request by a user, such as where the user provides a minimum percentage of change trigger that must be exceeded in order to automatically update the inventory levels for each compartment.

Having received initial system parameters from a user for configuring the ADMs 110, the inventory management system 130 may then determine appropriate amounts of inventory of items for forward deployment to compartments in the ADMs 110 used as distributed stores (e.g., in patient care areas). The inventory management system 130 may consider any combination of retrospective item utilization data, present (or "current") item utilization data, or predicted (or "projected") item utilization data. The inventory management system 130 may thus assist the facility 102 such as a hospital in effectively and efficiently managing patient care needs, while at the same time minimizing waste and maximizing financial dollars for the facility 102. For example, if a greater supply of an item is needed than is on hand at the facility 102, the inventory management system 130 can recommend or even send a request to the supplier 120 to supply an additional amount of the item determined based on inventory usage data.

Inventory determinations made for an item in one or many compartments in an automated dispensing machine in a particular area with reference to retrospective item utilization data are based on the utilization of the item for the particular area for a set period of time. An average daily usage of the item is then calculated based on the retrospective item utilization data, and the average daily usage is used to calculate a minimum days on hand of inventory of the item and a maximum days on hand of inventory of the item. The minimum days on hand value indicates a number of days' supply of the item needed in the compartment to prevent a stock-out of the item before a refill of the item is delivered from a below minimum warning being triggered.

The maximum days on hand value indicates the number of days of inventory turn for the item and the number of days that inventory for the item will be on hand before utilized.

For example, the inventory management system 130 may evaluate a listing of items to be loaded into a particular ADM 110 and then generate a recommended list of MAX and MIN values for items on the list that have exceeded a threshold (set by a user) number of doses dispensed in a month or a threshold (set by a user) number of patients in a month. As yet another example, a compartment may be loaded based on cumulative orders for a set period of days. The inventory management system 130 can recommend an item not currently in a distributed store ADM 110 (e.g., in a patient care area) to be added to a distributed store ADM 110 in a particular area (e.g., to become floor stock) if a certain number of orders for the item in the particular area have occurred over a certain time period. The item is then loaded to the ADM 110 in the particular area, and may not be unloaded until usage of the item indicates otherwise.

Inventory determinations made for an item in a compartment in a particular area with reference to present item utilization data permits near real-time management of inventory based on current patient needs (e.g., physician orders) and demands. Such inventory determinations are reactive to demands that are generated based on, for example, physician orders. An action may be triggered for an item that was ordered but that does not already exist in the forward deployed inventory. An action may be also triggered for an item that is ordered and exists in the forward deployed inventory, but the current quantity of the item available in the compartment does not meet the liabilities that are now created based on the new physician order.

For example, an order for a medical item (e.g., a medication) for a patient in a floor or other care area is evaluated by the inventory management system 130 to identify a number of doses a day (e.g., by frequency and dose) for the medical item. Then, after identifying a historical median or average length of stay for past patients associated with the medical item in that care area, the inventory management system 130 calculates the total doses of the medical item needed for the hospital stay of the patient. The calculation is be used to determine MIN and MAX value calculations for the medical item as stored in a compartment of an ADM 110 in the patient's care area. If an order for the same medical item is received for another patient, the inventory management system 130 then updates the calculated MIN and MAX values for the compartment to compensate for the total number of days of therapy for both patients based on average length of stay.

Inventory determinations made for an item in a compartment in a particular area with reference to predicted item utilization data can be based on, for example, typical patient diagnoses (e.g., DRG, ICD-9, ICD-10) for a particular area, standard physician order sets, average length of stay, and seasonal patterns for that area. The inventory management system 130 may thus operate in a near real-time mode, which, based on patient diagnosis codes, the inventory management system 130 could proactively react to potential needs for an item (e.g., for a patient).

In certain aspects, when the inventory management system 130 considers any combination of retrospective item utilization data, present item utilization data, or predicted item utilization data, the inventory management system 130 can use therapeutic substitution to change inventory utilization from a first item to a second item normalized for typical dosing and strength equivalence. Thus, if the facility 102 experiences a shortage or change in formulary of the first item, then the usage data of the first item can be applied to the second item based on their equivalence.

In addition to determining appropriate amounts of inventory of items for forward deployment to compartments in the ADMs 110 used as distributed stores upon receipt of initial system parameters from the user for configuring the ADMs 110, the inventory management system 130 may also determine an amount of inventory for the item for an ADM 110 used as a centralized store (e.g., in a pharmacy of the facility 102). For instance, the inventory management system 130 may consider various dimensions and data when calculating inventory for the centralized store ADM 110. The days of inventory of an item on hand as determined by a user will be applied if all distributed storage compartments are at their designated inventory levels. As another example, if an item has a history of being short filled based on a certain length of shortage from a suppliers, the inventory management system 130 may automatically increase the stock amount of the item to be stored in the centralized store ADM 110. As a further example, if the inventory management system 130 falls behind on a quantity on hand of an item below a set threshold (e.g., a certain number of days of stock for the item), the inventory management system 130 may send a notification (e.g., to a pharmacist or administrator) indicating a potential inability to supply the item to the distributed store ADMs 110.

As yet another example, the inventory management system 130 may set the days on hand value for an item with a short expiration timeframe to be lower than an item having a longer expiration timeframe in order to minimize waste. As a further example, the inventory management system 130 can determine a value indicative of days of inventory on hand for an item based on the item's lead time. For instance, a longer lead time will increase both the amount of the item to be reordered and the number of days to keep the item on hand. As a further example, the inventory management system 130 may adjust the days of inventory on hand for an item based on the item's cost and override determined inventory needs for the item. In such instances, a critical minimum value may be set for the item that indicates an amount of the item that is needed on hand to treat a certain number of patients for a certain time period based on replenishment lead time for the item.

In certain aspects, the values calculated by the inventory management system 130 when determining appropriate amounts of inventory of items for forward deployment to compartments in the ADMs 110 used as distributed stores and appropriate amounts of inventory of items for ADM(s) 110 used as a centralized store may conflict with the values indicated in the initial system parameters for the ADMs 110 from the user. This may occur where a user sets a MIN value (e.g., a minimum number of stock of an item required to prevent a stock-out of the item in a compartment) for an item in a compartment in an ADM 110 that is less than a MIN value calculated by the inventory management system 130 that indicates a greater amount of the item should be in stock in the ADM 110 based on retrospective item usage data.

For example, if a MIN and MAX value calculated by the inventory management system 130 for an item in a compartment falls within the user-defined range of the compartment's pocket minimum and pocket maximum, and optionally the calculated MIN and MAX values exceed a preset percentage change threshold defined by the user, the inventory management system 130 can overwrite the user-defined MIN and MAX values to the newly calculated values. As another example, if the newly calculated MIN value is less than the user-defined pocket minimum (e.g., a minimum number of items that should be stored in a compartment of an ADM 110), then the inventory management system 130 may continue to utilize the user-defined pocket minimum value for the compartment. As yet another example, if a newly calculated MAX value for a compartment exceeds the pocket maximum value, a notification (e.g., to an exception queue) may be provided by the inventory management system 130 to an administrator or other user indicating the difference, and optionally suggesting another or larger sized compartment or alternatively a sequential drain type scenario. The inventory management system 130 may further automatically pend the item based on a decision made by the user (e.g., whether to change the user-defined MAX value) in response to the notification.

As a further example, if stock of an item in an ADM 110 exceeds a user-defined threshold for a number of days without removal and the item is further not a commonly (or "standard") stocked item for the ADM 110, then the inventory management system 130 may provide a notification (e.g., to an exception queue) to have the item unloaded from the ADM 110. The user can either accept or reject this recommendation. As yet a further example, if the inventory management system 130 determines that there is an item not stocked in an ADM 110 that meets or exceeds a need for a scheduled time period, then the inventory management system 130 may send a notification to load stock of the item to the ADM 110 and optionally suggest a particular compartment in the ADM, a MIN value for the compartment, and a MAX value for the compartment. The user may accept or reject the suggestion.

After the inventory management system 130 initializes an ADM 110 with initial system parameters provided by a user and determines appropriate amounts of inventory of items for forward deployment to compartments in the ADM 110, the inventory management system 130 may then continue to monitor item usage for the ADM 110 in order to update or otherwise change the inventory amounts for the ADM 110. For example, the inventory management system 130 may monitor the occurrence and frequency of stock-outs of an item for a particular ADM 110. The inventory management system 130 may then recommend, based on a past number of days of utilization, different MAX and MIN inventory levels for the item. If the different MAX value exceeds the pocket maximum for the compartment, the inventory management system 130 may identify or otherwise recommend a different or additional compartment for storage of the item in the ADM 110.

As another example, the inventory management system 130 may on a daily or other scheduled basis calculate average daily use for items based on historical utilization of the item for a certain number of days set by a user. The inventory management system 130 may then look for days in the set review period where the maximum number of an item used exceeded the average daily use of the item. The maximum number of the item used may be used to adjust the MIN value if necessary in order to prevent a stock-out of the item on a high utilization day. The user may determine a number for the minimum days the user wants the item to be stocked in the ADM 110 before the inventory management system 130 triggers a refill. The user may also determine the number of days the user wants the item to be in stock in a compartment in the ADM 110, and this determination may indicate a frequency at which the compartment should be refilled. For instance, if the user wants the item to be in stock for a minimum of three days and a maximum of seven days, the inventory management system 130 may multiply these values by the average daily usage of the item to determine the inventory levels for the item in the ADM 110.

In certain aspects, the inventory management system 130 will query the patient care area storage spaces nightly to determine if the storage location can support the next 24 hours of dispensing. When assessing how to facilitate care and minimize stock-outs, the inventory management system 130 may assess the designated inventory levels to determine if the inventory levels need to be adjusted to better match the needs of the medication storage location, and the inventory management system 130 may determine if a stock-out will happen within the next 24 hours based on current patient orders for the item. If a stock-out is likely to occur, the inventory management system 130 will then trigger a refill message for the item with a due time to prevent a stock-out that could interrupt patient care. In certain aspects, the inventory management system 130 will monitor diagnosis codes and average length of stay.

In certain aspects, the inventory management system 130 can be hosted by one or many servers. The servers can be any device having an appropriate processor, memory, and communications capability for hosting the inventory management system 130. The ADMs 110 to which the inventory management system 130 is connected over the network 150 can be considered clients in a client-server architecture with the inventory management system 130. The network 150 can include, for example, any one or more of a personal area network (PAN), a local area network (LAN), a campus area network (CAN), a metropolitan area network (MAN), a wide area network (WAN), a broadband network (BBN), the Internet, and the like. Further, the network 150 can include, but is not limited to, any one or more of the following network topologies, including a bus network, a star network, a ring network, a mesh network, a star-bus network, tree or hierarchical network, and the like.

Figure 2:
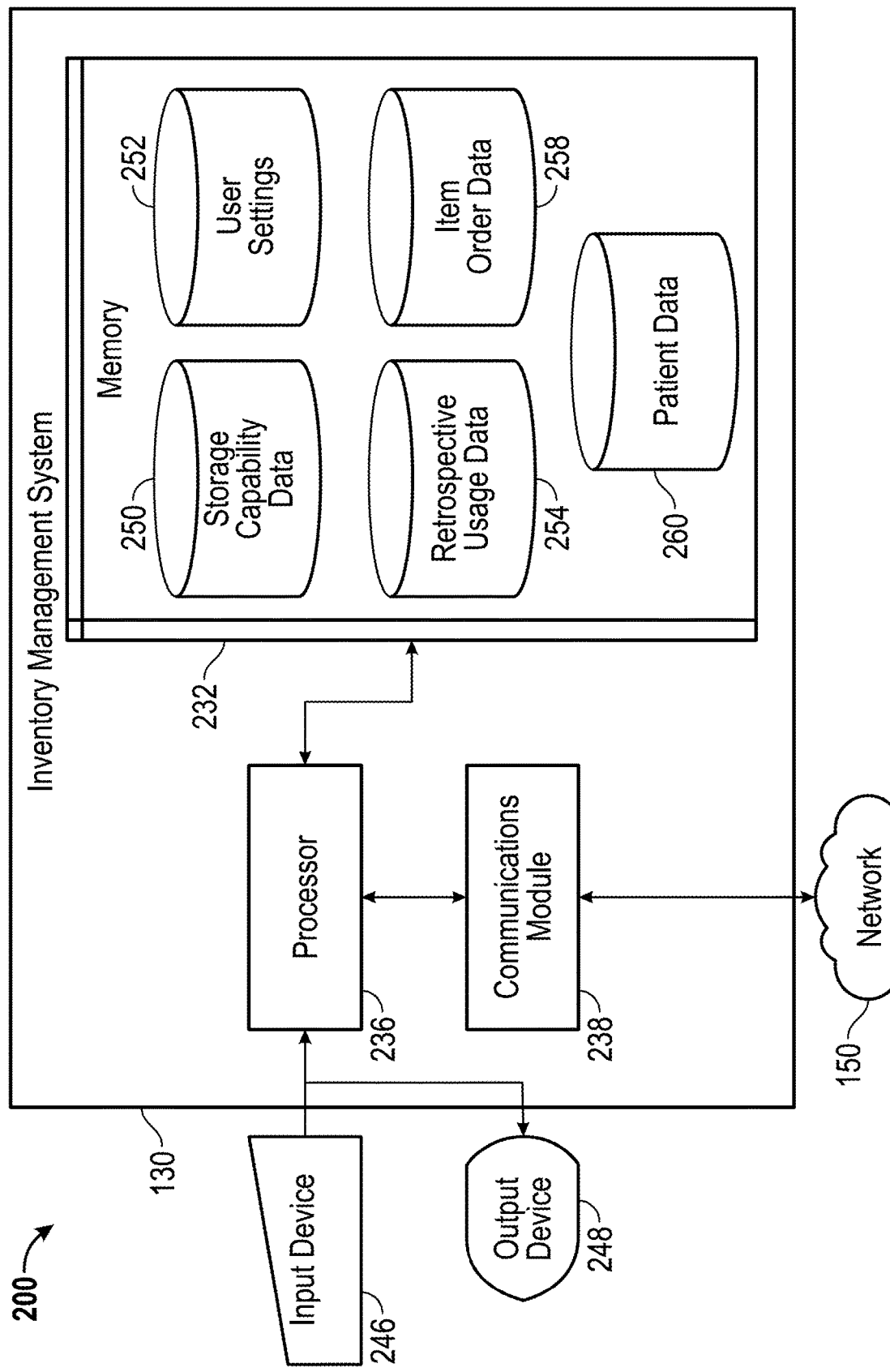
FIG. 2 is a block diagram illustrating the inventory management system of FIG. 1 according to certain aspects of the disclosure.

FIG. 2 is a block diagram 200 illustrating an example inventory management system 130 in the architecture 100 of FIG. 1 according to certain aspects of the disclosure. The inventory management system 130 is connected to the network 150 (e.g., to communicate with ADMs 110 connected to the network) via a communications module 238. The communications module 238 is configured to interface with the network 150 to send and receive information, such as data, requests, responses, and commands to other devices on the network. The communications module 238 can be, for example, a modem or Ethernet card.

The inventory management system 130 includes a processor 236, a communications module 238, and a memory 232. The memory includes storage capability data 250, user settings 252, retrospective usage data 254, item order data 258, and patient data 260. The storage capability data 250 includes the pocket minimum and pocket maximum values set for each compartment, whether defined by a user or determined by the inventory management system 130. The user settings 252 include the user-provided initial system parameters as well as authorization and identification data for appropriate users. The retrospective usage data 254 includes data of retrospective usage, current (or real-time) usage, and predicted usage for items, such as a daily average use of an item from a compartment and a daily maximum use of the item from the compartment. The item order data 258 includes information indicative of previous, current, and projected future orders for items (e.g., from doctors) and the specifics of the orders. The patient data 260 includes data indicative of a history of previous and current patients, including items associated with the patients (e.g., their medications, dosages, and schedules) such as an average length of stay for a patient associated with a particular item and an average number of patients associated with an item that are admitted during a time period.

The processor 236 of the inventory management system 130 is configured to execute instructions, such as instructions physically coded into the processor 236, instructions received from software in memory 240, or a combination of both. For example, the processor 236 of the inventory management system 130 executes instructions to receive an indicator of a minimum time period for which to stock an item in an ADM 110, and determine, based on the minimum time period for which to stock the item, the storage capability data 250, and the retrospective usage data 254, a minimum number of stock of the item to store in a compartment in the ADM 110. The processor 236 also executes instructions to provide a notification (e.g., to an output device 248) indicating the determined minimum number of stock of the item to store in the compartment.

For example, under this retrospective item utilization analysis, a user has defined for an item (e.g., Drug A) in a compartment that the pocket maximum is 25, the pocket minimum is three, a minimum of two days' supply of the item should be stored, and a maximum of seven days' supply of the item should be stored. The retrospective usage data 254 indicates that the item is dispensed an average of two times a day from the compartment, and the most the item was dispensed was three times in a day. The inventory management system 130 may then send a notification indicating that the new MIN value of the item is four (=2×2), which is the greater of: the daily average (=2) times the minimum days of supply set by the user (=2); the pocket minimum (=3); and the daily maximum (=3) for the item. In certain aspects, the processor 236 is further configured to send a request for additional stock for the item (e.g., either to a centralized store ADM 110 or to the supplier 120) when the determined minimum number of stock of the item to store in the compartment is less than the current stock of the item in the compartment.

In certain aspects, the processor 236 is configured to change a user-defined MIN (e.g., the minimum number of stock of the item to store) for a compartment to the MIN determined (e.g., based on the minimum time period for which to stock the item, the storage capability data 250, and the retrospective usage data 254) by the inventory management system 130 when the determined MIN is greater than the user-defined current MIN. The processor 236 may also update the user-defined MIN based on an average daily item usage indicated by a new order (e.g., indicated in the item order data 258), a number of new orders of the item, and a value indicating a minimum number of days before the item is reordered, and determine a MAX value for the item in the compartment based on the average daily item usage, the number of new orders of the item, and an average length of stay patients associated with the item. If the MAX value exceeds a pocket maximum for a compartment for the item, the processor 236 is configured to either provide a notification indicating or assign another compartment in the ADM 110 for storage of the item.

For example, under this present item utilization analysis (e.g., near real-time management occurs based on a new physician order), a user has defined for an item, Drug A, in a compartment that the pocket maximum is 25, and that the minimum number of days before the item is to be reordered is two days. The patient data 260 indicates that the average length of stay for a patient in the same care area for Drug A is five days, and that Drug A is dosed as a 5 mg tablet taken once a day at 4:00 PM and without a stop date. The inventory management system 130 may update the user-defined MIN to a determined MIN value of two, which is the average daily doses needed (=1) times the number of patient orders (=1) times the minimum number of days before reorder (=2). The inventory management system 130 set the MAX value of five, which is the average daily doses needed (=1) times the number of patient orders (=1) times the average length of stay in days (=5).

If an order for the same item for another patient is received, the inventory management system 130 can evaluate the item order data 258 and adjust the MIN and MAX values to accommodate the other patient. For instance, two more patients are admitted to the same care area as the patient in the immediately preceding example, and the two patients have been prescribed Drug A at the same dose. The inventory management system 130 then updates the MIN value to six, which is the average daily doses needed (=1) times the number of patient orders (=3) times the minimum number of days before reorder (=2). The inventory management system 130 updates the MAX value to fifteen, which is the average daily doses needed (=1) times the number of patient orders (=3) times the average length of stay (=5). The inventory management system 130 is also configured to adjust the MAX and MIN values upon discontinuance of a medication or when a patient is discharged from the facility 102. For instance, if a patient is discharged on day two, the inventory management system 130 would change the MIN to four and MAX to twelve.

In certain aspects, the processor 236 is also configured to determine a care area average daily item usage for the item based on the individual average daily item usage for the item (e.g., from the retrospective usage data 254) and the average number of patients associated with the item that are admitted during the time period (e.g., from the patient data 260). The processor 236 may then update the MIN value for stock of the item to store in the compartment based on the care area average daily item usage for the item and the minimum time period for which to stock the item. The processor 236 is further configured to determine a MAX value for stock of the item to store in the compartment based on the care area average daily item usage for the item and a maximum time period for which to stock the item.

For example, under this predictive item utilization analysis, inventory calculations by the inventory management system 130 may be based on a typical patient diagnosis (e.g., diagnosis-related group, International Statistical Classification of Diseases and Related Health Problems codes such as the ICD-9 and ICD-10) for a particular care area, standard physician order sets, average length of stay, and seasonal patient history patterns for that care area. The predictive analysis method may be used for an initial set up of an ADM 110.

For instance, a user has defined for an item, Drug A, in a compartment of an ADM 110 that the pocket maximum is 25, the pocket minimum is three, the minimum days on hand is two days, and the maximum days on hand is seven days. The patient data 260 indicates that for that care area the average length of stay for a patient taking Drug A is seven days, the average number of patients admitted to that care area on a weekly basis with a diagnosis requiring Drug A is ten patients, and Drug A is to be dosed at one tablet per day. Based on this information, the inventory management system 130 calculates that the average daily doses needed for patients on Drug A is ten, which is the doses per day of Drug A (=1) times the average number of patients admitted per week that require drug A (=10). The inventory management system 130 further calculates the inventory values for Drug A in the compartment of the ADM 110 should be a MIN of 20, which is the average daily doses needed (=10) times the minimum days on hand (=2), and a MAX of 70, which is the average daily doses needed (=10) times the maximum days on hand (=7). Given that the user-defined pocket maximum for the compartment for Drug A is 25, the MAX value of 70 indicates that three such compartments should be assigned for Drug A to accommodate predicted patient needs, and a notification or assignment may be made by the inventory management system 130 accordingly.

Figure 3:
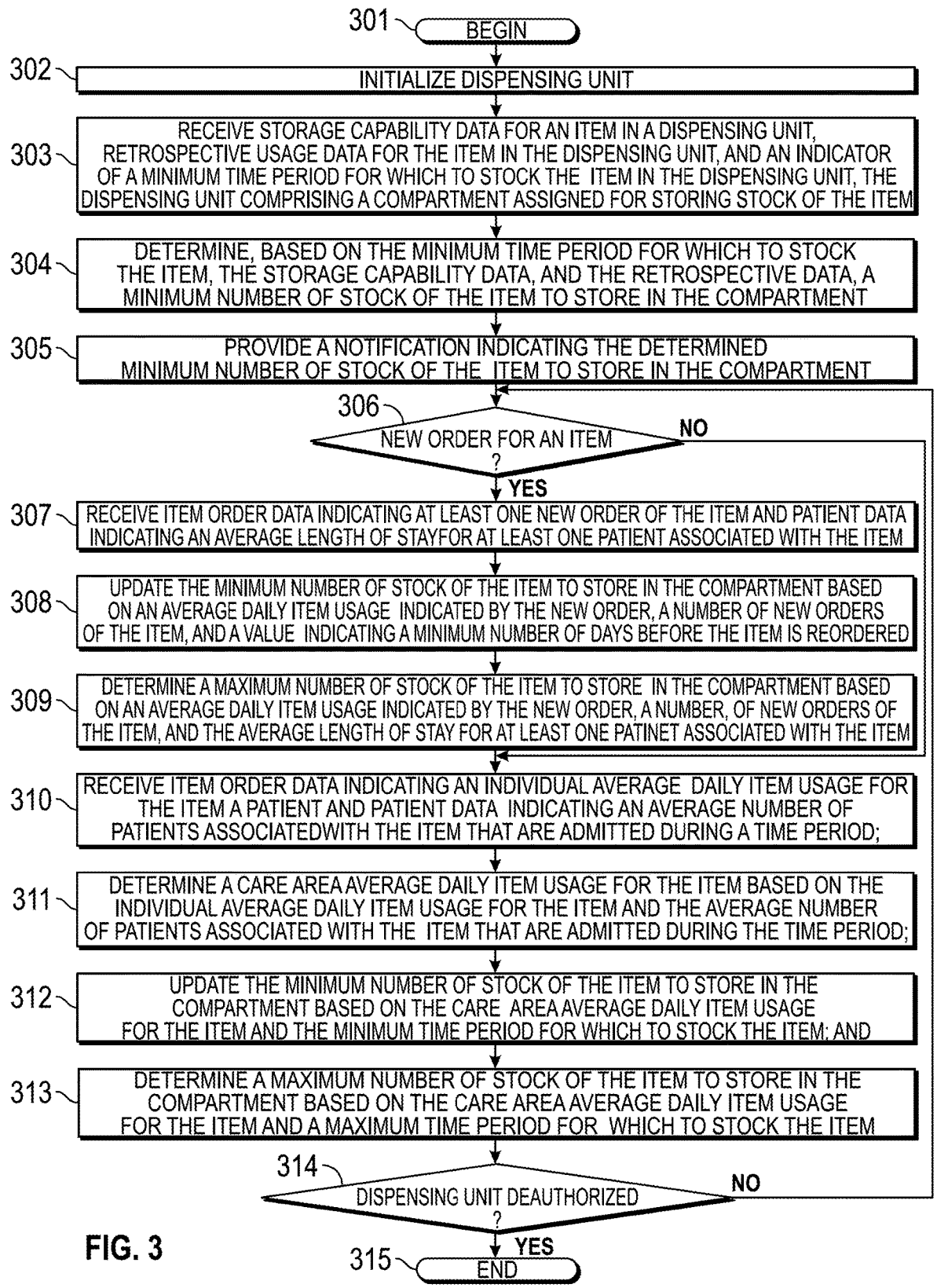
FIG. 3 illustrates an example process for automated inventory management using the example inventory management system of FIG. 2.

FIG. 3 illustrates an example process 300 for automated inventory management using the example inventory management system 130 of FIG. 2. While FIG. 3 is described with reference to FIG. 2, it should be noted that the process steps of FIG. 3 may be performed by other systems. The process 300 begins initially with a retrospective item usage analysis by proceeding from beginning step 301 to step 302 when an ADM 110 including a compartment assigned for storing stock of an item is initialized. Next, in step 303, the inventory management system 130 receives storage capability data 250 for the item in the compartment of the ADM 110, retrospective usage data 254 for the item in the ADM 110, and an indicator of a minimum time period for which to stock the item in the ADM 110. In step 304, the inventory management system 130 determines, based on the minimum time period for which to stock the item, the storage capability data 250, and the retrospective usage data 254, a minimum number of stock of the item to store in the compartment, and in step 305 provides a notification indicating the determined minimum number of stock of the item to store in the compartment.

Next, in decision step 306, a determination is made whether a new order for an item has been indicated to the inventory management system 130. If a new order for an item is indicated in decision step 306, the process 300 proceeds to step 307 for a current item usage analysis, otherwise the process 300 proceeds to step 310 for updating previously determined inventory values.

In step 307, the inventory management system 130 receives item order data 258 indicating at least one new order of the item, and patient data 260 indicating an average length of stay for at least one patient associated with the item. Next, in step 308, the minimum number of stock of the item to store in the compartment is updated based on an average daily item usage indicated by the new order, a number of new orders of the item, and a value indicating a minimum number of days before the item is reordered. In step 309, the inventory management system 130 determines a maximum number of stock of the item to store in the compartment based on an average daily item usage indicated by the new order, a number of new orders of the item, and the average length of stay for at least one patient associated with the item.

Proceeding to step 310 from either step 306 or step 309, in step 310 the inventory management system 130 receives item order data 258 indicating an individual average daily item usage for the item by a patient and patient data 260 indicating an average number of patients associated with the item that are admitted during a time period. In step 311, the inventory management system 130 determines a care area average daily item usage for the item based on the individual average daily item usage for the item and the average number of patients associated with the item that are admitted during the time period, and in step 312 updates the minimum number of stock of the item to store in the compartment of the ADM 110 based on the care area average daily item usage for the item and the minimum time period for which to stock the item. In step 313, the inventory management system 130 determines a maximum number of stock of the item to store in the compartment based on the care area average daily item usage for the item and a maximum time period for which to stock the item, and the process 300 proceeds to decision step 314.

In decision step 314, if a determination is made that the ADM 110 is not deauthorized (e.g., the ADM 110 is powered on and in use), then the process 300 returns to step 306, otherwise if a determination is made in decision step 314 that the ADM 110 is deauthorized, the process 300 ends in step 315.

Figure 4:
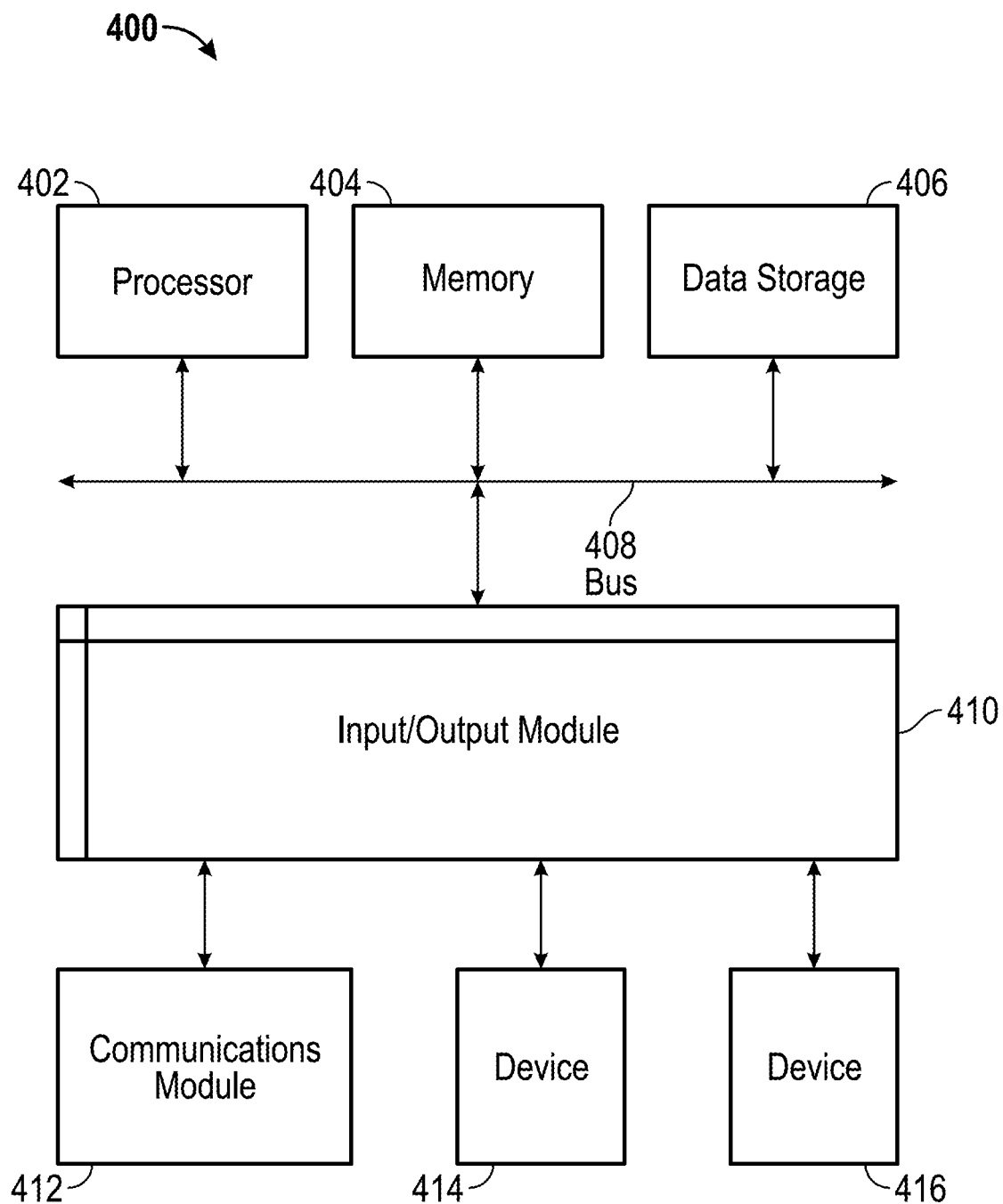
FIG. 4 is a block diagram illustrating an example computer system with which the inventory management system of FIG. 2 can be implemented.

FIG. 4 is a block diagram illustrating an example computer system 400 with which the inventory management system 130 of FIGS. 1 and 2 can be implemented. In certain aspects, the computer system 400 may be implemented using hardware or a combination of software and hardware, either in a dedicated server, or integrated into another entity, or distributed across multiple entities.

Computer system 400 (e.g., inventory management system 130) includes a bus 408 or other communication mechanism for communicating information, and a processor 402 (e.g., processor 236) coupled with bus 408 for processing information. By way of example, the computer system 400 may be implemented with one or more processors 402. Processor 402 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 400 can include, in addition to hardware, code that creates an execution environment for the computer program in question, e.g., code that constitutes processor firmware, a protocol stack, a database management system, an operating system, or a combination of one or more of them stored in an included memory 404 (e.g., memory 232), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 408 for storing information and instructions to be executed by processor 402. The processor 402 and the memory 404 can be supplemented by, or incorporated in, special purpose logic circuitry.

The instructions may be stored in the memory 404 and implemented in one or more computer program products, i.e., one or more modules of computer program instructions encoded on a computer readable medium for execution by, or to control the operation of, the computer system 400, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side vile languages, procedural languages, reflective languages, rule-based languages, scripting languages, stack-based languages, synchronous languages, syntax handling languages, visual languages, wirth languages, embeddable languages, and xml-based languages. Memory 404 may also be used for storing temporary variable or other intermediate information during execution of instructions to be executed by processor 402.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 400 further includes a data storage device 406 such as a magnetic disk or optical disk, coupled to bus 408 for storing information and instructions. Computer system 400 may be coupled via input/output module 410 to various devices (e.g., ADMs 110). The input/output module 410 can be any input/output module. Example input/output modules 410 include data ports such as USB ports. The input/output module 410 is configured to connect to a communications module 412. Example communications modules 412 (e.g., communications module 238) include networking interface cards, such as Ethernet cards and modems. In certain aspects, the input/output module 410 is configured to connect to a plurality of devices, such as an input device 414 (e.g., input device 246) and/or an output device 416 (e.g., output device 248). Example input devices 414 include a keyboard and a pointing device, e.g., a mouse or a trackball, by which a user can provide input to the computer system 400. Other kinds of input devices 414 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 416 include display devices, such as a LED (light emitting diode), CRT (cathode ray tube), or LCD (liquid crystal display) screen, for displaying information to the user.

According to one aspect of the present disclosure, the inventory management system 130 can be implemented using a computer system 400 in response to processor 402 executing one or more sequences of one or more instructions contained in memory 404. Such instructions may be read into memory 404 from another machine-readable medium, such as data storage device 406. Execution of the sequences of instructions contained in main memory 404 causes processor 402 to perform the process steps described herein. One or more processors in a multi-processing arrangement may also be employed to execute the sequences of instructions contained in memory 404. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 150) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 400 can include clients and servers. A client and server are generally remote from each other and typically interact through a communication network. The relationship of client and server arises by virtue of computer programs running on the respective computers and having a client-server relationship to each other. Computer system 400 can be, for example, and without limitation, a desktop computer, laptop computer, or tablet computer. Computer system 400 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 402 for execution. Such a medium may take many forms, including, but not limited to, non-volatile media, volatile media, and transmission media. Non-volatile media include, for example, optical disks, magnetic disks, or flash memory, such as data storage device 406. Volatile media include dynamic memory, such as memory 404. Transmission media include coaxial cables, copper wire, and fiber optics, including the wires that comprise bus 408. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A system for automated inventory management of a healthcare item dispensing unit for a healthcare facility, the system comprising:
   a memory comprising storage capability data for the dispensing unit, the dispensing unit comprising a first compartment assigned for storing stock of a plurality of items of an item type; and
   one or more processors configured to:
      monitor real time usage of the plurality of items of the item type;
      automatically determine, based on monitoring the real time usage over a period of time, a minimum time period for which to stock a supply of the item type in the dispensing unit before a refill request is triggered for the item type;
      receive an order for the item type, wherein the order includes a request for a plurality of item units;
      based on monitoring the real time usage of the plurality of items of the item type, and in response to receiving the order:
         determine a length of stay in a care area for at least one patient associated with the item type;
         determine at least a current usage of the item type during a first period of time within the care area of the at least one patient;
         determine a number of patients admitted to the care area during a second period of time; and
         determine a minimum number of stock of the item type to store in the first compartment of the dispensing unit based on the determined length of stay, a number of new orders for the item type, the determined current usage of the item type during the first period of time within the care area, the determined number of patients admitted to the care area during a second period of time, and the minimum time period for which to stock the item supply;
      automatically determine a first maximum number of stock of the item type that can be stored in the first compartment based on a volumetric space of an item unit of the item type when loaded into the first compartment;
      automatically determine a second maximum number of stock of the item type that can be stored in a second compartment of the dispensing unit based on the determined first maximum number, the volumetric space of the item unit when loaded into the first compartment, and a change of volume between the first and second compartments;
      automatically provide, in response to determining the minimum number of stock of the item type, a notification to a device remote from the system indicating the minimum number of stock of the item type to store in the first compartment;
      determine a number of stock of the item type to store in the first compartment; and
      if the number of stock of the item type to store in the first compartment exceeds the first maximum number of stock of the item type that can be stored the first compartment, provide a notification assigning the second compartment for storage of one or more of the item units based on the determined second maximum number.

2. The system of claim 1, wherein the one or more processors is further configured to send a request for additional stock for the item type when the minimum number of stock of the item type to store in the first compartment is less than a current stock of the item type in the compartment.

3. The system of claim 1, wherein the minimum time period comprises a minimum number of days for which to have the item type in stock in the dispensing unit.

4. The system of claim 1, wherein the storage capability data comprises a user-defined minimum number of stock of the item type to store in the first compartment.

5. The system of claim 4, wherein the one or more processors is further configured to change the user-defined minimum number of stock of the item type to store in the first compartment to the determined minimum number of stock of the item type to store in the first compartment when the determined minimum number of stock of the item type to store in the first compartment is greater than a threshold defined by the user.

6. The system of claim 1, wherein the one or more processors are further configured to:
   determine, based on the real time over a period of time usage, at least one of a daily average use of the item type from the first compartment or a daily maximum use of the item from the first compartment.

7. The system of claim 1, wherein the length of stay includes an average length of stay, and wherein the number of stock of the item type to store in the compartment is determined based on an average daily item usage indicated by the order and the average length of stay.

8. The system of claim 1, wherein the length of stay includes an individual average daily item usage for the item type, and wherein the one or more processors is further configured to:
   determine a care area average daily item usage for the item type based on the individual average daily item usage for the item type and an average number of patients associated with the item that are admitted during the second period of time;
   update the minimum number of stock of the item type to store in the first compartment based on the care area average daily item usage for the item type and the minimum time period for which to stock the item type;
   wherein the number of stock of the item type to store in the first compartment is determined based on the care area average daily item usage for the item type and a maximum time period for which to stock the item type.

9. A method for automated inventory management of a healthcare item dispensing unit for a healthcare facility, the method comprising:
   monitoring real time usage of a plurality of items of an item type associated with care of patients in a care area;
   automatically determine, based on monitoring the real time usage over a period of time, a minimum time period for which to stock a supply of the item type in the dispensing unit before a refill request is triggered for the item type;
   receive an order for the item type, wherein the order includes a request for a plurality of item units;
   based on monitoring the real time usage of the plurality of item of the item type, and in response to receiving the order:
      determining a length of stay in the care area for at least one patient associated with the item type;
      determining a current usage of the item type during a first period of time within the care area;
      determining a number of patients admitted to the care area during a second period of time; and
      determining a minimum number of stock of the item type to store in a first compartment of the dispensing unit based on the determined minimum time period for which to stock the item supply, a storage capability of the dispensing unit, the determined length of stay, a number of new orders for the item type, the determined current usage of the item type during a first period of time within the care area, and the determined number of patients admitted to the care area during a second period of time;
   automatically determining a first maximum number of stock of the item type that can be stored in the first compartment of the dispensing unit based on a volumetric space of an item unit of the item type when loaded into the first compartment;
   automatically determining a second maximum number of stock of the item type that can be stored in a second compartment of the dispensing unit based on the determined first maximum number, the volumetric space of the item unit when loaded into the first compartment, and a change of volume between the first and second compartments;
   automatically providing, in response to determining the minimum number of stock of the item type, by the one or more computing devices, a notification to a device remote from the one or more computing devices, indicating the minimum number of stock of the item type to store in the first compartment;
   determining a number of stock of the item type to store in the first compartment; and
   if the number of stock of the item type to store in the first compartment exceeds the first maximum number of stock of the item type that can be stored the first compartment, provide a notification assigning the second compartment for storage of one or more of the item units based on the determined second maximum number.

10. The method of claim 9, further comprising sending a request for additional stock for the item type when the minimum number of stock of the item type to store in the first compartment is less than a current stock of the item type in the first compartment.

11. The method of claim 9, wherein the minimum time period comprises a minimum number of days for which to have the item in stock in the dispensing unit.

12. The method of claim 9, wherein the storage capability comprises a user-defined minimum number of stock of the item type to store in the first compartment.

13. The method of claim 12, further comprising changing the user-defined minimum number of stock of the item type to store in the first compartment to the determined minimum number of stock of the item type to store in the first compartment when the determined minimum number of stock of the item type to store in the first compartment is greater than a threshold defined by the user.

14. The method of claim 9, further comprising:
   determining, based on the real time over a period of time usage data, at least one of a daily average use of the item type from the compartment or a daily maximum use of the item type from the compartment.

15. The method of claim 9, wherein the length of stay is an average length of stay, the method further comprising:
   updating the minimum number of stock of the item type to store in the first compartment based on an average daily item usage for the item type, a number of the new orders of the item of the item type, and a value indicating a minimum number of days before the item type is reordered; and wherein the maximum number of stock of the item type to store in the first compartment is determined based on an average daily item usage indicated by the order and the average length of stay for at least one patient associated with the item type.

16. The method of claim 9, wherein the length of stay is an average length of stay, the method further comprising:

determining a care area average daily item usage for the item type based on an individual average daily item usage for the item type and an average number of patients associated with the item that are admitted during the second period of time;

updating the minimum number of stock of the item type to store in the compartment based on the care area average daily item usage for the item type and the minimum time period for which to stock the item type; and determining a maximum number of stock of the item type to store in the first compartment based on the care area average daily item usage for the item type and a maximum time period for which to stock the item type.

17. A non-transitory machine-readable storage medium comprising machine-readable instructions for causing a processor to execute a method for automated inventory management of a healthcare item dispensing unit for a healthcare facility, the method comprising:

monitoring real time usage of a plurality of items of an item type associated with care of patients in a care area;

automatically determine, based on monitoring the real time usage over a period of time, a minimum time period for which to stock an item supply of the item type in the dispensing unit before a refill request is triggered for the item type;

receive an order for the item type, wherein the order includes a request for a plurality of item units;

based on monitoring the real time usage of the plurality of items of the item type, and in response to receiving the order:

determining a length of stay in the care area for at least one patient associated with the item type;

determining a current usage of the item type during a first period of time within the care area;

determining a number of patients admitted to the care area during a second period of time; and determining a minimum number of stock of the item type to store in a first compartment of the dispensing unit based on the determined minimum time period for which to stock the item supply, a storage capability of the dispensing unit, the determined length of stay, a number of new orders for the item type, the determined current usage of the item type during a first period of time within the care area, and the determined number of patients admitted to the care area during a second period of time;

automatically determine a first maximum number of stock of the item type that can be stored in the first compartment of the dispensing unit based on a volumetric space of an item unit of the item type when loaded into the first compartment;

automatically determine a second maximum number of stock of the item that can be stored in a second compartment of the dispensing unit based on the determined first maximum number, the volumetric space of the item unit when loaded into the first compartment, and a change of volume between the first and second compartments;

automatically providing, in response to determining the minimum number of stock of the item type, by the one or more computing devices, a notification to a device remote from the one or more computing devices, indicating the minimum number of stock of the item type to store in the compartment;

determining a number of stock of the item type to store in the first compartment; and if the number of stock of the item type to store in the first compartment exceeds the first maximum number of stock of the item type that can be stored the first compartment, provide a notification assigning the second compartment for storage of the item type based on the determined second maximum number.

18. The method of claim 9, further comprising:

causing the dispensing unit to deploy the first compartment for storing at least the minimum number of stock of the item type.

19. The non-transitory machine readable medium of claim 17, the method further comprising:

causing the dispensing unit to deploy the first compartment for storing at least the minimum number of stock of the item type.

20. The system of claim 1, wherein the one or more processors are further configured to:

determining that there is a respective item unit of a respective item not stocked in the dispensing unit that meets or exceeds a need for a scheduled time period; and sending, based on determining that the respective item unit is not stocked, a notification to load stock of the respective item type to the dispensing unit, including a suggestion of a particular compartment to load the stock of the respective item type, a minimum number of stock of the respective item type to store in the particular compartment, and a maximum number of stock of the respective item type that can be stored in the particular compartment; and receiving, after sending the notification, a user acceptance or rejection of the compartment.

21. The system of claim 1, wherein the one or more processors are further configured to:

cause the dispensing unit to deploy the compartment for storing at least the minimum number of stock of the item type.

* * * * *